(12) United States Patent
Chia et al.

(10) Patent No.: US 10,722,308 B2
(45) Date of Patent: Jul. 28, 2020

(54) OPTICAL FIBERS AND ASSOCIATED SYSTEMS

(71) Applicant: Boston Scientific Scimed, Inc., Maple Grove, MN (US)

(72) Inventors: Wen-Jui Ray Chia, Sunnyvale, CA (US); Steven Yihlih Peng, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 80 days.

(21) Appl. No.: 16/025,145

(22) Filed: Jul. 2, 2018

(65) Prior Publication Data

US 2019/0008589 A1  Jan. 10, 2019

Related U.S. Application Data

(60) Provisional application No. 62/529,322, filed on Jul. 6, 2017.

(51) Int. Cl.
 *A61B 18/22* (2006.01)
 *A61B 18/26* (2006.01)
 *A61B 18/00* (2006.01)

(52) U.S. Cl.
 CPC .............. *A61B 18/22* (2013.01); *A61B 18/26* (2013.01); *A61B 2018/00982* (2013.01); *A61B 2018/2205* (2013.01); *A61B 2018/2244* (2013.01); *A61B 2018/2272* (2013.01)

(58) Field of Classification Search
 CPC ................................. A61B 18/22; A61B 18/26
 See application file for complete search history.

(56) References Cited

U.S. PATENT DOCUMENTS

| | | | |
|---|---|---|---|
| 5,257,991 A | 11/1993 | Fletcher et al. |
| 5,354,294 A | 10/1994 | Chou |
| 5,509,917 A | 4/1996 | Cecchetti et al. |
| 5,562,657 A | 10/1996 | Griffin |

(Continued)

FOREIGN PATENT DOCUMENTS

WO   WO 2010/075368 A1   7/2010

OTHER PUBLICATIONS

International Search Report and Written Opinion for corresponding International Application No. PCT/US2018/040552, dated Oct. 1, 2018 (10 pages).

*Primary Examiner* — William J Levicky
(74) *Attorney, Agent, or Firm* — Bookoff McAndrews, PLLC

(57) ABSTRACT

One described aspect is an optical fiber comprising: a fiber core that extends along a fiber axis, is configured to transmit a laser energy along the fiber axis, and terminates at a distal end with an angled distal face; a jacket that surrounds a proximal portion of the fiber core along the fiber axis, and terminates at a distal end located proximal of the angled distal face; a fiber tip including a proximal end with an angled distal face; and a reflector including a proximal face attached to the angled distal face of the fiber core, a distal face attached to the angled proximal face of the fiber tip, and at least one layer configured to direct the laser energy out of the fiber core along a laser axis generally transverse with the fiber axis, wherein the optical fiber tapers along the fiber axis. Associated laser systems are also disclosed.

20 Claims, 3 Drawing Sheets

(56) References Cited

U.S. PATENT DOCUMENTS

| | | | |
|---|---|---|---|
| 5,983,900 A * | 11/1999 | Clement | A61B 18/203 |
| | | | 128/898 |
| 9,289,262 B2 | 3/2016 | Hanley et al. | |
| 9,488,782 B2 | 11/2016 | Griffin | |
| 9,788,898 B2 | 10/2017 | Zerfas | |
| 9,810,844 B2 | 11/2017 | Reever | |
| 2008/0294154 A1 * | 11/2008 | Ibrahim | A61B 18/1492 |
| | | | 606/13 |
| 2010/0016845 A1 | 1/2010 | Hanley et al. | |
| 2011/0255828 A1 | 10/2011 | Sudarshanam | |
| 2012/0157982 A1 * | 6/2012 | Anderson | A61B 18/22 |
| | | | 606/16 |
| 2014/0088575 A1 * | 3/2014 | Loeb | A61B 18/24 |
| | | | 606/16 |
| 2014/0126876 A1 | 5/2014 | Li et al. | |
| 2015/0272676 A1 * | 10/2015 | Hasenberg | A61B 18/22 |
| | | | 606/15 |
| 2017/0042618 A1 | 2/2017 | Brown | |
| 2017/0128133 A1 * | 5/2017 | Pinnow | A61B 18/22 |

* cited by examiner

OPTICAL FIBERS AND ASSOCIATED SYSTEMS

CROSS-REFERENCE TO RELATED APPLICATIONS

This application claims the benefit of priority to U.S. Provisional Application No. 62/529,322, filed Jul. 6, 2017, which is incorporated by reference herein in its entirety.

TECHNICAL FIELD

Aspects of the present disclosure generally relate to optical fibers and associated laser systems. Particular aspects relate to distal aspects of optical fibers for medical laser systems.

BACKGROUND

Optical fibers may be used in medical laser systems to deliver a laser energy to a treatment site. Many such optical fibers include a fiber core with a distal end surrounded by a cap. Some caps include a reflective surface configured to direct the laser energy away from the fiber core, and an air pocket distal of the reflective surface. Because most reflective surfaces cannot reflect all of the laser energy, the air pocket is often required to achieve total reflection of the laser energy. To accommodate the air gap, most caps typically have an outer diameter larger than an outer diameter of the fiber core, resulting in an enlarged bulbous shape at the distal end of the fiber. Most caps include an exit port for the laser energy. In some instances, the exit port may include a lens or other aperture that further increases the outer diameter of the cap, and/or creates other irregularities in the enlarged bulbous shape.

In some noninvasive medical procedures, a scope may be advanced through a body toward a body cavity, and the optical fiber may be advanced distally through a working channel of the scope until the cap is adjacent a target in the body cavity, such as a kidney stone in a kidney. The inner diameter of the working channel must be sized to accommodate the larger diameter and/or enlarged bulbous shape of the cap, thereby requiring a larger working channel. Irregularities of the enlarged bulbous shape may further increase the requisite size of the working channel. A larger channel may be undesirable, especially considering that most scopes include other working channels competing for a limited amount of space inside of the scope.

The optical fibers and associated laser systems described herein address these problems and other deficiencies in the prior art.

SUMMARY

One aspect of the present disclosure is an optical fiber. The optical fiber may comprise: a fiber core that extends along a fiber axis, is configured to transmit a laser energy along the fiber axis, and terminates at a distal end with an angled distal face; a jacket that surrounds a proximal portion of the fiber core along the fiber axis, and terminates at a distal end located proximal of the angled distal face; a fiber tip including a proximal end with an angled proximal face; and a reflector including a proximal face attached to the angled distal face of the fiber core, a distal face attached to an angled proximal face of the fiber tip, and at least one layer configured to direct the laser energy out of the fiber core along a laser axis generally transverse with the fiber axis. An outer diameter of the jacket may be greater than an outer diameter of the fiber core, and an outer diameter of the fiber tip may be equal to or less than the outer diameter of the fiber core.

According to this aspect, the proximal face of the reflector may be attached to the angled distal face of the fiber core without creating an air gap therebetween. The distal face of the reflector may be attached to the angled proximal face of the fiber tip without creating an air gap therebetween. For example, the entire proximal face of the reflector may be attached to the angled distal face of the fiber core, and the entire distal face of the reflector may be attached to the angled proximal face of the fiber tip.

The angled distal face of the fiber core may be bonded to the proximal face of the reflector by a first adhesive; the laser energy may have a first absorption rate with a stone or tissue and a second absorption rate with the first adhesive; and the first absorption rate may be higher than the second absorption rate. Furthermore, the angled distal face of the reflector may be bonded to the angled proximal face of the fiber tip by a second adhesive; the laser energy may have a third absorption rate with the second adhesive; and the first absorption rate may be higher than the third absorption rate. The first adhesive may be different from the second adhesive, and the third absorption rate may be higher than the second absorption rate. The laser energy may have a fourth absorption rate with the fiber tip, and the fourth absorption rate may be higher than the third absorption rate.

The reflector may be configured to direct at least 90% of the laser energy out of the fiber core along the laser axis. The least one reflecting layer may include a dielectric material or a metallic material. For example, the metallic material may include at least one of aluminum, gold, or silver. A distal end of the fiber tip may include an atraumatic shape. The optical fiber may include a buffer extending along the fiber axis between the fiber core and the jacket. For example, the buffer may be a coating applied to at least a proximal portion of the fiber core. Any optical fiber described herein may be part of system, wherein the distal end of the jacket defines a distal stop surface, and the system comprises a scope including a working channel configured to movably receive the jacket, and a proximal stop surface engageable with the distal stop surface of the jacket to limit a movement of the optical fiber in the working channel.

Another aspect of the present disclosure is an optical fiber comprising: a fiber core that extends along a fiber axis, is configured to transmit a laser energy along the fiber axis, and terminates at a distal end with an angled distal face; a jacket that surrounds a proximal portion of the fiber core along the fiber axis, and terminates at a distal end located proximal of the angled distal face; a buffer extending along the fiber axis between the fiber core and the jacket; a fiber tip including a proximal end with an angled proximal face; and a reflector including a proximal face attached to the angled distal face of the fiber core, a distal face attached to the angled proximal face of the fiber tip, and at least one layer configured to direct the laser energy out of the fiber core along a laser axis generally transverse with the fiber axis.

An outer diameter of the jacket may be greater than an outer diameter of the fiber core, and an outer diameter of the fiber tip may be equal to or less than the outer diameter of the fiber core. The buffer may terminate at a distal end located between the distal end of the jacket and the distal end of the fiber core. In some aspects, the proximal face of the reflector may be attached to the fiber core by a first layer of adhesive, and the distal face of the reflector may be attached to the fiber tip by a second layer of adhesive. The first and second layers of adhesive may be different.

Yet another aspect of the present disclosure is a system comprising: an optical fiber including: a fiber core that extends along a fiber axis, is configured to transmit a laser energy along the fiber axis, and terminates at a distal end with an angled distal face; a jacket that surrounds a proximal portion of the fiber core along the fiber axis, and terminates at a distal end located proximal of the angled distal face; a fiber tip including a proximal end with an angled proximal face; and a reflector including a proximal face attached to the angled distal face of the fiber core, a distal face attached to the angled proximal face of the fiber tip, and at least one layer configured to direct the laser energy out of the fiber core along a laser axis generally transverse with the fiber axis. The distal end of the jacket may define a distal stop surface, an outer diameter of the jacket may be greater than an outer diameter of the fiber core, and an outer diameter of the fiber tip may be equal to or less than the outer diameter of the fiber core. The system may further comprise a scope including a working channel configured to movably receive the jacket, and a proximal stop surface engageable with the distal stop surface of the jacket to limit a movement of the optical fiber in the working channel.

The proximal face of the reflector may be attached to the angled distal face of the fiber core without creating an air gap therebetween, and the distal face of the reflector may be attached to the angled proximal face of the fiber tip without creating an air gap therebetween. The working channel may include a proximal portion having an inner diameter configured to receive the outer diameter of the jacket, and a distal portion having an inner diameter configured to receive the outer diameters of the fiber body and the fiber tip. The distal stop surface of the jacket may be engageable with the proximal stop surface of the working channel to limit movement of the optical fiber in the working channel. For example, the optical fiber may be movable between: a retracted position, wherein the distal stop surface of the jacket is spaced apart from the proximal stop surface of the working channel; and an extended position, wherein the distal stop surface of the jacket is at or adjacent the stop surface of the working channel. As a further example, the fiber tip may be fully retracted into the distal portion of the working channel when the optical fiber is in the retracted position.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows.

DETAILED DESCRIPTION

Aspects of the present disclosure are now described with reference to optical fibers and associated laser systems. Some aspects are described with reference to medical procedures where laser energy is used to treat a stone. References to a particular type of procedure, laser energy, stone, and/or bodily organ are provided for convenience and not intended to limit the present disclosure unless claimed. Accordingly, the concepts described herein may be utilized for any analogous fiber—medical or otherwise.

Numerous axes and directions are described. Each axis may be transverse, or even perpendicular, with the next so as to establish a Cartesian coordinate system with an origin point O. One axis may extend along a longitudinal axis of an element. Relative locations and directions may be indicated by the terms "proximal" and "distal," and their respective initials "P" and "D." Proximal refers to a position closer to the exterior of the body or a user, whereas distal refers to a position closer to the interior of the body or further away from the user. Appending the initials P or D to an element number signifies a proximal or distal location, and appending P or D to an arrow in a figure signifies a proximal or distal direction along an axis. The term "elongated" may refer to any object that is substantially longer in relation to its width, such as an object having a length that is at least two times longer than its width along its longitudinal axis. Some elongated objects, for example, are axially extending in a proximal or distal direction along an axis. Unless claimed, these terms are provided for convenience and not intended to limit this disclosure to a particular location, direction, or orientation.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." Conversely, the terms "consists of" and "consisting of" are intended to cover an exclusive inclusion, such that a device or method that consists of a list of elements includes only those elements. Terms such as "generally," "about," "substantially," and/or "approximately" indicate a range of possible values that are within +/−5% of a stated value.

Figure 1A:
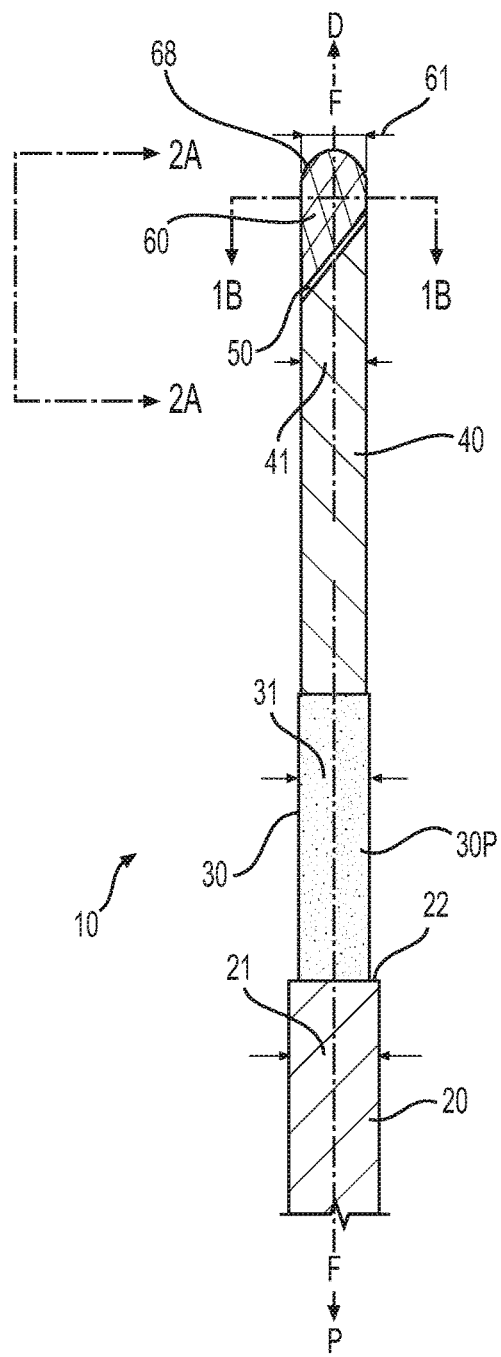
FIG. 1A depicts a distal end of an exemplary optical fiber.

One aspect of the present disclosure is an optical fiber 10 extending along a fiber axis F-F. As shown in FIG. 1A, optical fiber 10 may comprise: a jacket 20; a buffer 30; a fiber core 40; a reflector 50; and a fiber tip 60. As described further below, these elements may be configured such that an outer diameter 21 of jacket 20 is greater than an outer diameter 41 of fiber core 40; an outer diameter 31 of buffer 30 is greater than diameter 41 of fiber core 40; and an outer diameter 61 of fiber tip 60 is equal to or less than diameter 41. In this configuration, optical fiber 10 may be described as tapering or stepping-down from a larger dimension to a smaller dimension in a proximal-to-distal direction along fiber axis F-F.

Jacket 20 may comprise one or more layers surrounding proximal portions of buffer 30 and/or fiber core 40 along fiber axis F-F. In some aspects, jacket 20 may be made of a polymeric material that is attached to buffer 30 along its length. Jacket 20 of FIG. 1A, for example, terminates at a distal end that is located proximal of a distal end of buffer 30, and/or proximal of a distal end of fiber core 40. Because outer diameter 21 is larger than outer diameters 31 and 41, the distal end of jacket 20 may define a distal stop surface 22. For example, distal stop surface 22 may be formed by cutting a portion of jacket 20 away from optical fiber 10.

Buffer 30 may comprise one or more layers surrounding fiber core 40. In some aspects, buffer 30 may be made of a material that is dielectric, highly reflective, and/or biocompatible, such as a polymeric material. Buffer 30 may be configured to mechanically isolate fiber core 40 from jacket 20, and/or further promote internal reflection of the laser energy. In some aspects, buffer 30 may comprise a tube surrounding fiber core 40 (e.g., a "loose buffer"); while in others, buffer 30 may comprise a coating applied to fiber core 40 (e.g., a "tight buffer"). For example, as shown in FIG. 1A, buffer 30 may comprise a thin coating applied to fiber core 40 so that outer diameter 31 of buffer 30 is only nominally greater (e.g., 1% to 3%) than outer diameter 41 of fiber core 40. The thin coating may, for example, comprise or consist of a dielectric biocompatible fluoropolymer.

Figure 2A:
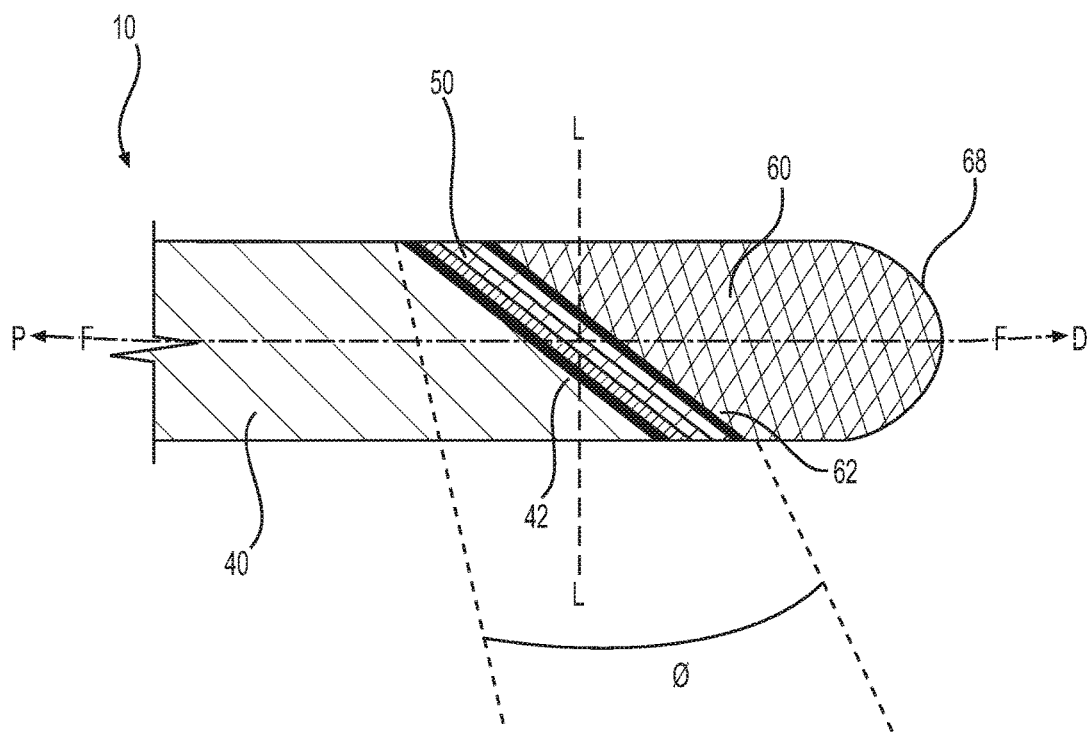
FIG. 2A depicts a side view of the optical fiber of FIG. 1A taken at Section 2A-2A of FIG. 1A.
Figure 2B:
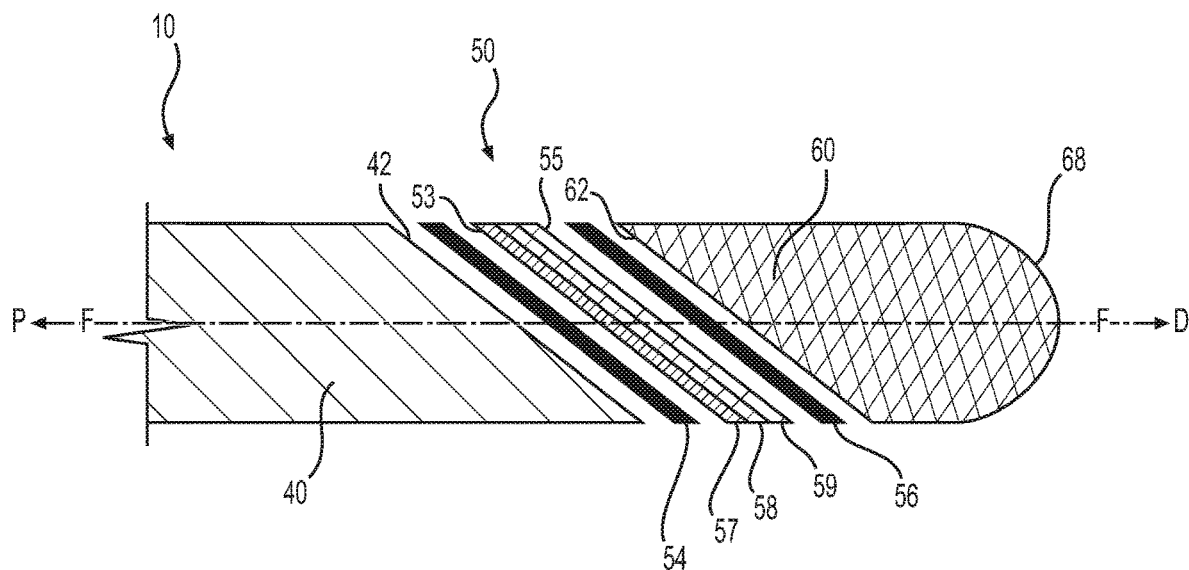
FIG. 2B depicts an exploded side view of the fiber of FIG. 2A.

Fiber core 40 of FIG. 1A may comprise one or more optical fibers configured to deliver the laser energy. A cladding may surround portions of fiber core 40, and/or buffer 30 may comprise the cladding. To minimize outer diameter 41, fiber core 40 may consist of a single optical fiber made of a glass material and/or a polymeric material. As shown in FIGS. 2A-B, the distal end of fiber core 40 may include an angled distal face 42 that is generally transverse with optical fiber axis F-F (e.g., at a 45° angle, or an angle between 30° and 60°). As described further below, angled distal face 42 may be engageable with reflector 50. For example, all or a portion of angled distal face 42 may be chemically and/or mechanically bonded to reflector 50.

Reflector 50 of FIG. 2A may be configured to direct the laser energy out of fiber core 40 along a laser axis L-L that is generally transverse with the fiber axis F-F. As shown in the exploded section view depicted in FIG. 2B, for example, reflector 50 may have a composite body extending along fiber axis F-F between a proximal end including a proximal face 53, and distal end including a distal face 55. Proximal face 53 of reflector 50 may be attached to at least a portion of angled distal face 42 of fiber core 40. For example, as shown in FIG. 2B, the angled distal face 42 of fiber core 40 may be bonded to the proximal face 53 of reflector 50 by a first adhesive 54, and the angled proximal face 62 of fiber tip 60 may be bonded to the distal face 55 of reflector 50 by a second adhesive 56. Any type of adhesive may be used. The composite body of reflector 50 may comprise one or more layers that are arranged to reflect a substantial portion (e.g., 90% or greater), or substantially all (e.g., at least 99%), of the laser energy along laser axis L-L; and/or spread the laser energy across an exemplary distribution angle θ. The one or more layers may include any reflective materials.

In some aspects, the composite body of reflective 50 may be configured for use with specific laser energies, such as those commonly used in medical procedures. For example, as shown in FIG. 2B, the composite body may comprise: a first layer 57, a second layer 58, and a third layer 59. At least one of layers 57, 58, or 59 may include a dielectric material (e.g., a polymer, such as fluorocarbon polymer) and/or a metallic material (e.g., aluminum, gold, silver, or the like). Each successive layer 57, 58, and/or 59 may be stacked and/or fused together (e.g., by application of heat, pressure, or an adhesive) until reflector 50 achieves a minimum width along laser axis L-L (e.g., approximately 1 mm to 3 mm); and/or a corresponding minimum reflectivity (e.g., 90% or greater). According to these aspects, second layer 58 may include one or more metallic materials (the same or different), and first and second layers 57 and 59 may include one or more dielectric materials (the same or different) engageable with said metallic materials and/or one or more adhesive materials.

Figure 1B:
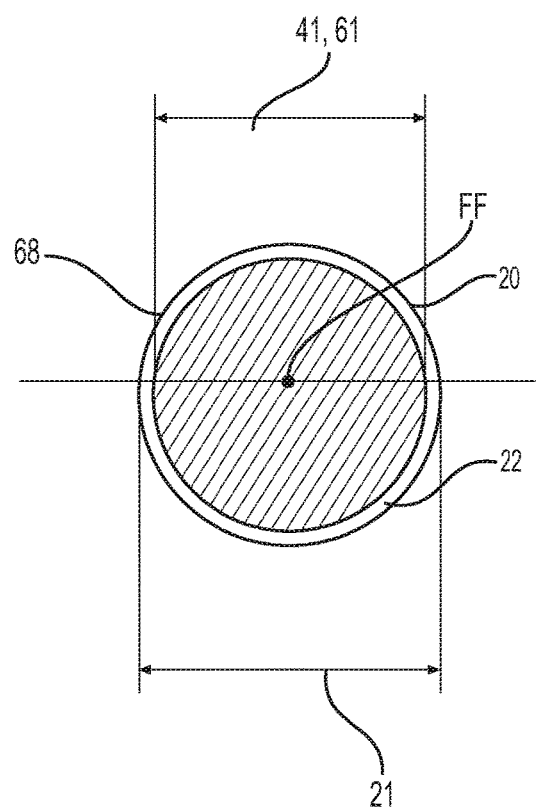
FIG. 1B depicts a cross-sectional view of the fiber of FIG. 1 taken at Section 1B-1B of FIG. 1A.

Fiber tip 60 may be configured to absorb and/or diffuse an amount of laser energy passing through reflector 50 along fiber axis F-F. As shown in FIGS. 2A-B, fiber tip 60 may include a solid body extending along fiber axis F-F between a proximal end including an angled proximal face 62, and a distal end including an atraumatic shape 68. As shown in FIG. 1B, for example, the solid body made of a crystalline material (e.g., sapphire); and/or may have a cylindrical shape with an outer diameter 61 that is equal to or less than outer diameter 41 of fiber core 40. Angled proximal face 62 of fiber tip 60 may be bonded to the with distal face 55 of reflector 50 by second adhesive 56. Because reflector 50 is configured to reflect substantial portions of the laser energy, angled proximal face 62 of fiber tip 60 may be attached to distal face 55 of reflector 50 without creating an air gap therebetween. For example, second adhesive 56 may comprise a continuous layer of adhesive and/or non-porous material that bonds the entire distal-facing surface of distal face 55 to the entire proximal-facing surface of angled proximal face 62, leaving no air gap therebetween. The air gap may no longer be required to achieve total reflection of the laser energy.

Atraumatic shape 68 may be formed integral with (e.g., FIGS. 2A-B). As shown, atraumatic shape 68 may comprise a semi-spherical shape configured for advancement into a body cavity along axis F-F in a proximal-distal direction with minimal risk of accidentally piercing a wall of the body cavity. Any similar shape may be used. Shape 68 may be a molded into the distal end fiber tip 60, or permanently or removably attached to tip 60.

Various aspects of attaching fiber core 40 to reflector 50, and/or reflector 50 to fiber tip 60 are described. One or more adhesives may be used. For example, first and second adhesives 54 and 56 may be made the same or different materials, of uniform or composite formulation. In some aspects, first and second adhesives 54 and 56 may both have low absorption rates with the laser energy; and first adhesive 54 may have the lowest absorption rate. For example, the laser energy may have a wavelength (e.g., 532 nm) that has a high absorption rate (e.g., 99% or greater) with a target (e.g., a tissue), and a low absorption rate (e.g., less than 1%) with first and second adhesives 54 and 56. This configuration allows the target to be rapidly heated by the laser energy without also rapidly heating adhesives 54 and/or 56, which may cause premature failure. As a further example, the laser energy may have an even lower absorption rate (e.g., less than 0.1%) with first adhesive 54, ensuring that a greater amount of the laser energy will be reflected by reflector 50, and not absorbed by first adhesive 54, generating heat.

First and second adhesives 54 and 56 may be uniformly applied. For example, when set, each adhesive 54 and 56 may have a disk-shape with a uniform thickness, as shown in 2B. The disk-shape may be preformed and configured to adhere reflector 50 to fiber core 40 and/or fiber tip 60 when heated. Alternative shapes are also contemplated. For example, first and second adhesives 54 and 56 may alternatively have a ring-shape with an outer diameter approximate to the outer diameter 41 of fiber core 40, and an inner diameter less than outer diameter 41, thereby defining an disk-shaped cavity. As before, the ring-shapes may be heated to adhere reflector 50 to fiber core 40 and/or fiber tip 60. A fluid (e.g., air) may be sealed in the disk-shaped cavities when the ring-shapes are heated.

Figure 3A:
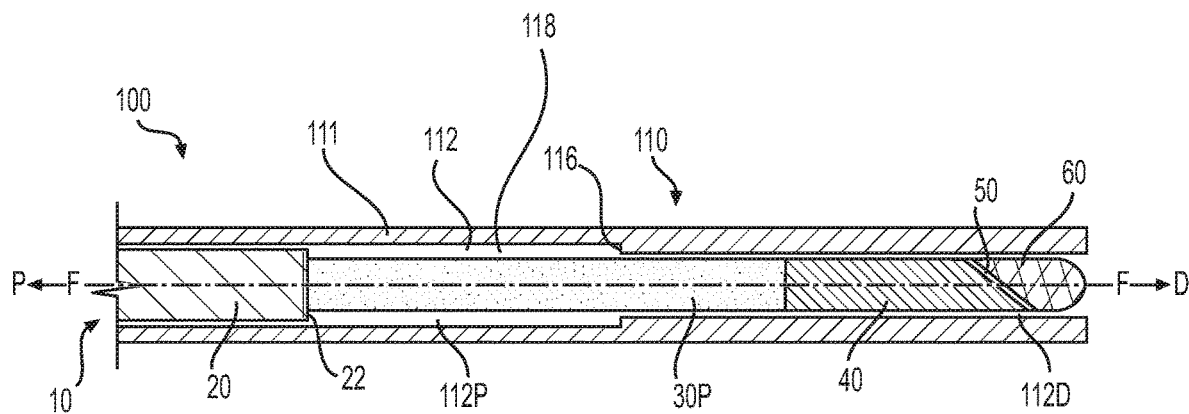
FIG. 3A depicts a section view of an exemplary optical fiber and scope, wherein a distal end of the fiber is retracted into a working channel of the scope.
Figure 3B:
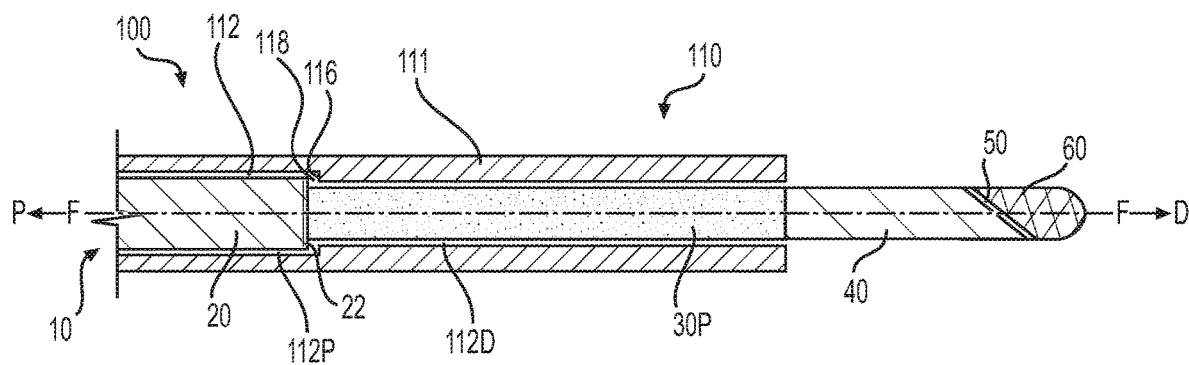
FIG. 3B depicts the optical fiber and scope of FIG. 3A, wherein the distal end of the fiber is extended out of the working channel of the scope.

An exemplary system 100 is now described. As shown in FIG. 3A-B, for example, system 100 may comprise any optical fiber 10 described herein, wherein the distal end of the jacket 20 defines the distal stop surface 22; and a scope 110 including a scope body 111 having a working channel 112 including a proximal stop surface 116. Working channel 112 may be configured to movably receive optical fiber 10. Proximal stop surface 116 engageable with the distal stop surface 22 of jacket 20 to limit a movement of optical fiber 10 inside working channel 112. Scope body 111 may comprise any elongated shape, such as a catheter. Working channel 112 of FIGS. 3A-B, for example, includes a proximal portion 112P having an inner diameter configured to receive outer diameter 21 of jacket 20, and a distal portion 112D having an inner diameter configured to receive the respective outer diameters 41 and 61 of fiber core 40 and fiber tip 60.

Because diameters 41 and/or 61 are smaller than diameter 21, as shown in FIG. 1A, proximal stop surface 116 may be a ledge formed at the transition from proximal portion 112P of working channel 112 to distal portion 112D of channel 112. In some aspects, the inner diameter of distal portion 112D of working channel 112 may be equal to the inner diameter of proximal portion 112P of channel 112, and stop surface 116 may be a protrusion extending towards axis F-F to define an inner diameter smaller than the inner diameters of portions 112P and 112D. As shown in FIGS. 3A-B, optical fiber 10 may be movable axially inside of working channel 112 between a proximal or retracted position (e.g. FIG. 3A), wherein distal stop surface 22 is spaced apart (e.g., proximally) from proximal stop surface 116; and a distal or extended position (e.g., FIG. 3B), wherein the distal stop surface 22 is at or adjacent proximal stop surface 16 to limit an axial movement of distal stop surface 22. Fiber 10 also may be rotated inside of channel 112.

Fiber tip 60 may be retracted into distal portion 112D of working channel 112 when optical fiber 10 is in the proximal position, and extended out of distal portion 112D when fiber 10 is in the distal position, thereby avoiding damage from over-extension. Proximal portion 112P of working channel 112 may define an interior cavity 118 with a volume the extends annularly around axis F-F, expands when optical fiber 10 is in the proximal position, and contracts when fiber 10 is the distal position. Additional elements of system 100 may be located within interior cavity 118 to further guide movements of optical fiber 10.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. An optical fiber comprising:
 a fiber core that extends along a fiber axis, is configured to transmit a laser energy along the fiber axis, and terminates at a distal end with an angled distal face;
 a jacket that surrounds a proximal portion of the fiber core along the fiber axis, and terminates at a distal end located proximal of the angled distal face;
 a fiber tip including a proximal end with an angled proximal face; and
 a reflector including a proximal face attached to the angled distal face of the fiber core, a distal face attached to the angled proximal face of the fiber tip, and at least one layer configured to direct the laser energy out of the fiber core along a laser axis generally transverse with the fiber axis,
 wherein an outer diameter of the jacket is greater than an outer diameter of the fiber core, and an outer diameter of the fiber tip is equal to or less than the outer diameter of the fiber core.

2. The optical fiber of claim 1, wherein the proximal face of the reflector is attached to the angled distal face of the fiber core without creating an air gap therebetween.

3. The optical fiber of claim 2, wherein the distal face of the reflector is attached to the angled proximal face of the fiber tip without creating an air gap therebetween.

4. The optical fiber of claim 1, wherein the reflector is configured to direct at least 90% of the laser energy out of the fiber core along the laser axis.

5. The optical fiber of claim 1, wherein the least one reflecting layer includes a dielectric material or a metallic material.

6. The optical fiber of claim 5, wherein the metallic material includes at least one of aluminum, gold, or silver.

7. The optical fiber of claim 1, wherein a distal end of the fiber tip includes an atraumatic shape.

8. The optical fiber of claim 1, wherein the fiber tip is a solid body.

9. The optical fiber of claim 1, wherein the fiber tip comprises a crystalline material.

10. The optical fiber of claim 1, wherein the reflector is configured to direct at least 99% of the laser energy out of the fiber core along the laser axis.

11. The optical fiber of claim 1, wherein the proximal face of the reflector is attached to the fiber core by a first layer of adhesive, and the distal face of the reflector is attached to the fiber tip by a second layer of adhesive.

12. An optical fiber comprising:
 a fiber core that extends along a fiber axis, is configured to transmit a laser energy along the fiber axis, and terminates at a distal end with an angled distal face;
 a jacket that surrounds a proximal portion of the fiber core along the fiber axis, and terminates at a distal end located proximal of the angled distal face;
 a buffer extending along the fiber axis between the fiber core and the jacket;
 a fiber tip including a proximal end with an angled proximal face; and
 a reflector including a proximal face attached to the angled distal face of the fiber core, a distal face attached to the angled proximal face of the fiber tip, and at least one layer configured to direct the laser energy out of the fiber core along a laser axis generally transverse with the fiber axis,
 wherein an outer diameter of the jacket is greater than an outer diameter of the fiber core, and an outer diameter of the fiber tip is equal to or less than the outer diameter of the fiber core.

13. The optical fiber of claim 12, wherein the buffer terminates at a distal end located between the distal end of the jacket and the distal end of the fiber core.

14. The optical fiber of claim 12, wherein the proximal face of the reflector is attached to the fiber core by a first layer of adhesive, and the distal face of the reflector is attached to the fiber tip by a second layer of adhesive.

15. A system comprising:
an optical fiber including:
- a fiber core that extends along a fiber axis, is configured to transmit a laser energy along the fiber axis, and terminates at a distal end with an angled distal face;
- a jacket that surrounds a proximal portion of the fiber core along the fiber axis, and terminates at a distal end located proximal of the angled distal face;
- a fiber tip including a proximal end with an angled proximal face; and
- a reflector including a proximal face attached to the angled distal face of the fiber core, a distal face attached to the angled proximal face of the fiber tip, and at least one layer configured to direct the laser energy out of the fiber core along a laser axis generally transverse with the fiber axis,
wherein the distal end of the jacket defines a distal stop surface, an outer diameter of the jacket is greater than an outer diameter of the fiber core, and an outer diameter of the fiber tip is equal to or less than the outer diameter of the fiber core; and
a scope including a working channel configured to movably receive the jacket, and a proximal stop surface engageable with the distal stop surface of the jacket to limit a movement of the optical fiber in the working channel.

16. The system of claim 15, wherein the proximal face of the reflector is attached to the angled distal face of the fiber core without creating an air gap therebetween, and the distal face of the reflector is attached to the angled proximal face of the fiber tip without creating an air gap therebetween.

17. The system of claim 15, wherein the working channel includes a proximal portion having an inner diameter configured to receive the outer diameter of the jacket, and a distal portion having an inner diameter configured to receive the outer diameters of the fiber body and the fiber tip.

18. The system of claim 17, wherein the distal stop surface of the jacket is engageable with the proximal stop surface of the working channel to limit movement of the optical fiber in the working channel.

19. The system of claim 18, wherein the optical fiber is movable between:
- a retracted position, wherein the distal stop surface of the jacket is spaced apart from the proximal stop surface of the working channel; and
- an extended position, wherein the distal stop surface of the jacket is at or adjacent the stop surface of the working channel.

20. The system of claim 19, wherein the fiber tip is fully retracted into the distal portion of the working channel when the optical fiber is in the retracted position.

* * * * *